United States Patent
Cole

[11] Patent Number: 5,534,003
[45] Date of Patent: Jul. 9, 1996

[54] METHOD OF REMOVING HAIR FROM A LOCALIZED AREA OF SKIN BY SURFACE ELECTROLYSIS

[76] Inventor: H. Lee Cole, 160 S. May St., Southern Pines, N.C. 28387

[21] Appl. No.: 370,017

[22] Filed: Jan. 9, 1995

[51] Int. Cl.$^6$ ............................. A61B 17/38; A61B 17/41
[52] U.S. Cl. .................................................. 606/36; 606/43
[58] Field of Search ......................................... 606/36, 43

[56] References Cited

U.S. PATENT DOCUMENTS

| | | | |
|---|---|---|---|
| 3,994,300 | 11/1976 | Siddons | 606/36 |
| 5,026,369 | 6/1991 | Cole | 606/36 |
| 5,470,332 | 11/1995 | Mehl, Sr. et al. | 606/36 |

FOREIGN PATENT DOCUMENTS 2595239  9/1987  France .................... 606/36

*Primary Examiner*—Lee S. Cohen

[57] ABSTRACT

The present invention relates to a method for removing hair from a localized area of a patient's skin through surface electrolysis. The method of the present invention is non-invasive in that the patient's skin is never penetrated by a needle or the like. In a preferred method of the invention, a ground terminal is placed on the skin proximate a selected localized treatment area from which hair is to be removed. Thereafter, an electrified probe terminal, which includes an absorbent material saturated with an electrode solution, is touched directly to a micro-area of skin within the localized treatment area while maintaining a close association between the electrified probe terminal and the ground terminal. Therefore, the electric current path between the probe and the ground is not a substantially greater length than the width of the localized treatment area. The electric current causes electrolysis of the hair follicles in the micro-area being treated. Thereafter, the electrified probe terminal may be moved to successive micro-areas within the localized treatment area to perform electrolysis of hairs in those micro-areas. After a selected time period of decomposition, the hairs can be easily removed from the patient's skin.

15 Claims, 2 Drawing Sheets

METHOD OF REMOVING HAIR FROM A LOCALIZED AREA OF SKIN BY SURFACE ELECTROLYSIS

FIELD OF THE INVENTION

The present invention relates to the field of electrolysis and particularly pertains to simultaneously removing a number of hairs from a localized area of skin through surface electrolysis.

BACKGROUND OF THE INVENTION

Hair removal through electrolysis has been performed for many years, and through this process, patients have been able to selectively remove hair from certain body areas. Ordinarily, this hair removal process is carried out by inserting an electrified needle into an individual hair follicle. This obviously can be a very painful ordeal and also is unduly time consuming, because only one hair is removed at a time. Typically, a patient is grounded by having the patient hold a ground terminal in her hand or by otherwise affixing a ground terminal a remote distance from the area to be treated by electrolysis. This results in electricity passing through a large area of the patient's body, which in some cases can cause efficiency and conductivity problems and can reduce the effectiveness of the electrolysis treatment. Often, repeat electrolysis treatment sessions are necessary to remove all unwanted hairs from a particular area.

In the early stages of electrolysis, there was much confusion and speculation as to why the process worked. Some investigators, for example, postulated that the hair follicle was "electrocuted". Later, it was determined that the process works because of electrolytic action that gives rise to chemical decomposition in the hair follicle.

Presently, the process of electrolysis as it relates to hair removal is well understood. Within each hair follicle, there is a solution of salt water that provides the chemicals for the electrolysis process to work. Specifically, subjecting the salt water solution to an electric current results in the salt (NaCl) and the water ($H_2O$) breaking into their constituent chemical elements. This process is referred to as electrolysis, and the subsequent rearrangement of the basic elements of salt and water is referred to as ionization. One of the new compounds that is formed as a result of the ionization is sodium hydroxide (NaOH). The sodium hydroxide produced is highly caustic to the hair follicle and causes the follicle to die through a decomposition process. The general epithelium of the follicle is killed, rendering the follicle unable to ever produce more hair. After the hair follicle has decomposed, the hair can be removed by an extraction process.

As shown in the patent to Cole (U.S. Pat. No. 5,026,369, hereinafter the "'369 patent"), the method of electrolysis may utilize an electrode solution as a medium for conducting current to the tissue and salt water content of the hair follicles. The electrode solution enhances conductivity because the skin surface and the hairs themselves are less effective conductors of electricity than is the electrode solution.

As pointed out above, hair removal through a conventional electrolysis method, where the skin is actually penetrated with a current-carrying needle, is very painful and slow. Therefore, a need exists for a less painful and more efficient method for removing unwanted hair. A previous attempt to address the problems inherent with traditional electrolysis resulted in the development of the non-invasive method of electrolysis disclosed in the Cole '369 patent.

While the '369 patent discloses an electrolysis method that is painless, the method disclosed in the '369 patent is almost as time-consuming as conventional electrolysis with a needle, because both methods only remove one hair at a time. The '369 patent discloses directing an electric current down an individual hair that has been coated with an electrode solution. The '369 patent does not disclose a method of removing a number of hairs from a localized area at the same time. Thus, a need exists for a hair removal method that is both painless and expeditious.

SUMMARY AND OBJECTS OF THE PRESENT INVENTION

The present invention relates to a non-invasive electrolysis method for eliminating a number of hairs from a localized area of skin at one time. The present method is non-invasive in that the process does not entail penetrating the patient's skin with a needle or the like. The present method is quicker than traditional electrolysis methods because many hair follicles can be destroyed at the same time. Unlike Cole's '369 patent, the present invention does not direct electric current along an individual hair to be removed. Instead, an electrified probe terminal, which has an absorbent tip saturated with an electrode solution, is touched directly to a localized area of skin to eliminate all of the hairs in that localized area. Also, unlike the '369 patent and other previous electrolysis methods, the ground terminal of the electrolysis device may be placed on the patient's skin in or in the vicinity of the localized area to be treated instead of being held in the patient's hand or otherwise remotely positioned. Maintaining this relatively close association between the probe and the ground substantially prevents the path of the electric current from extending beyond the boundaries of the localized treatment area. This oftentimes results in better conductivity and better electrical transmission to the hair follicles in the skin.

It is therefore an object of the present invention to provide an expeditious and painless electrolysis method for simultaneously removing a number of hairs from a localized area of skin.

Another object of the present invention is to provide a surface electrolysis method that is non-invasive in that the patient's skin is not penetrated by a needle.

Another object of the present invention is to provide an expeditious electrolysis method that entails touching a probe terminal directly to successive micro-areas of skin within the localized treatment area while transmitting an electric current through the probe.

A further object of the present invention is to provide a method of performing electrolysis on a localized area of skin wherein the ground terminal of an electrolysis device is engaged with the skin in or in the vicinity of the localized area so that the path of the electric current through the patient is essentially confined to the localized treatment area.

Another object of the present invention is to provide a method of performing electrolysis on a localized area of skin wherein there is maintained a relatively close association between the electrified probe terminal and the ground terminal so that during electrolysis, they are not separated by a distance substantially greater than the greatest width of the localized treatment area.

Another object of the present invention is to utilize an electrified probe terminal that includes a saturated absorbent material at the tip of the probe to apply an electrode solution onto the surface of the skin during the electrolysis method.

DETAILED DESCRIPTION OF THE INVENTION

Figure 1:
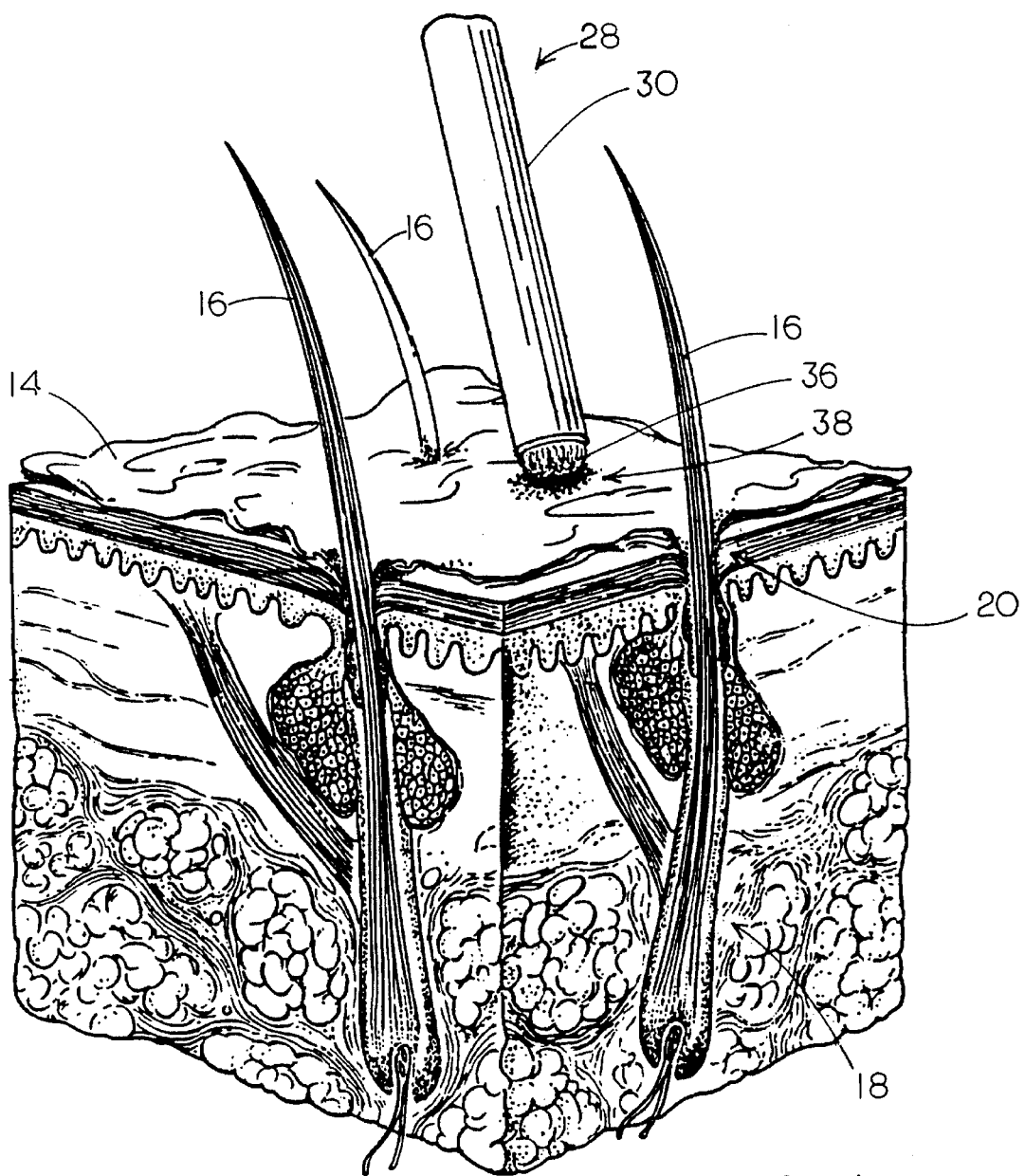
FIG. 1 is an illustration showing the structure of the skin and hair follicles and particularly showing the portion of the present electrolysis method where an electrified probe terminal having a saturated absorbent tip is touched directly to an area of skin from which hairs are to be removed.
Figure 2:
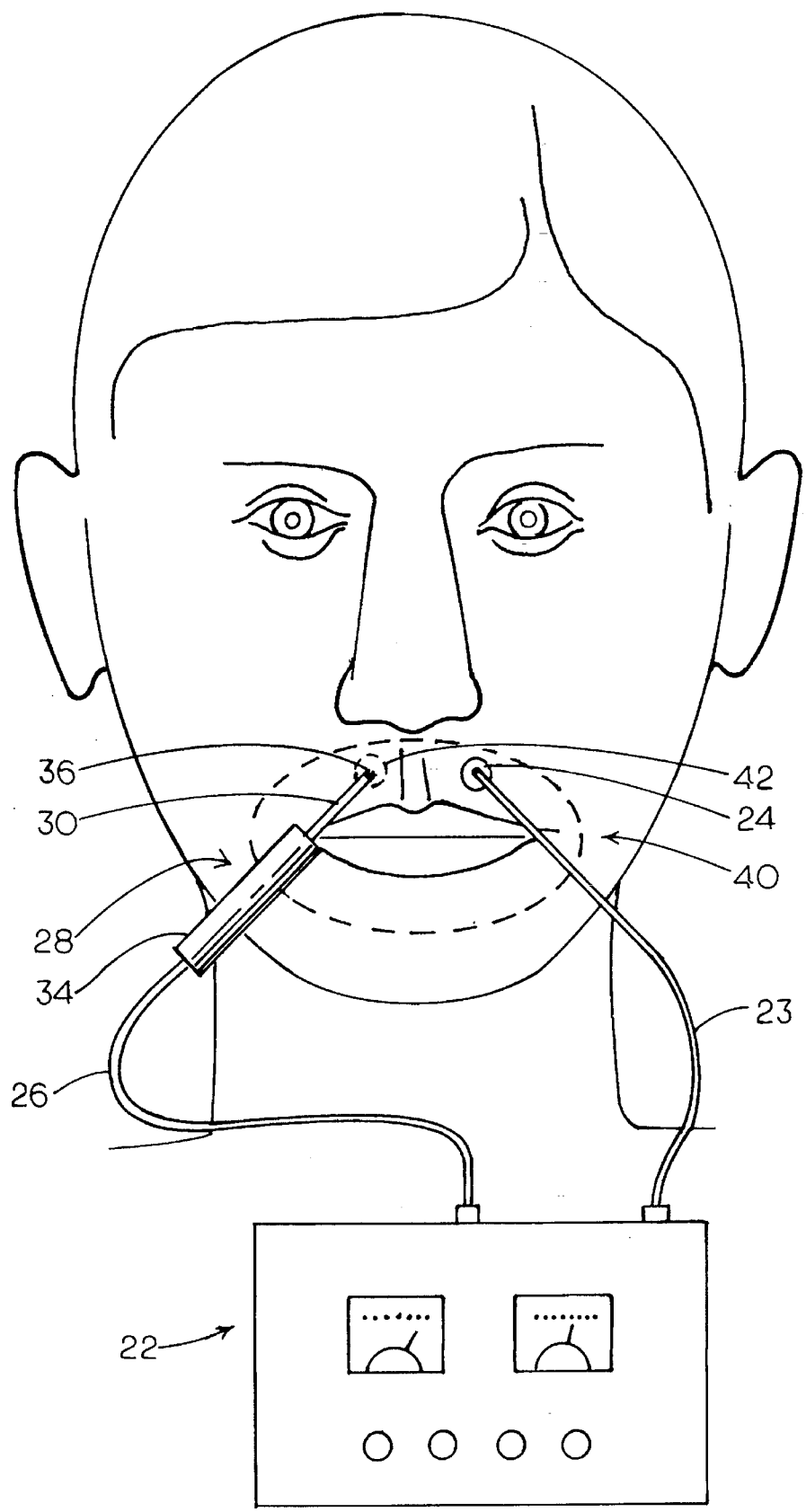
FIG. 2 is a schematic illustration showing the present electrolysis method being performed on a micro-area of skin within a localized treatment area wherein the ground terminal is engaged with the skin within the localized treatment area.

With further reference to the drawings, the present method of performing surface electrolysis on a localized treatment area is illustrated therein. Before proceeding with a discussion of the method itself, it will be beneficial to basically review the anatomical structure of the skin and hair. In this regard, the skin and hair structure of the patient is shown in a schematic or illustrative form. As shown in the drawings, the patient's skin surface is indicated by the numeral 14. Extending upwardly through the patient's skin surface 14 are hairs or hair shafts 16. Each hair shaft 16 extends downwardly through the skin and is anchored below the skin surface 14. The portion of the hair structure lying below the skin surface is referred to as the hair follicle and is indicated in the drawings by the numeral 18. Surrounding the hair shaft 16 about the surface of the skin 14 is what is referred to as soft moist tissue, which is indicated by the numeral 20. As will be further understood from subsequent portions of this disclosure, the soft moist tissue 20 in the present process acts as a conductor of electric current in the electrolysis process that forms the subject matter of the present invention.

To carry out the present method, it is required that there be an electric current source, such as a conventional current-producing electrolysis device, indicated in the drawings by the numeral 22. A desirable electrolysis device 22 has the capability of generating an electric current having a relatively low amperage and relatively high voltage (e.g. a current range of 1–5000 microamps and voltage of 100–400 volts). For example, a typical electrolysis device of this type is manufactured by A. R. Hinkle of Sun Valley, Calif., and is referred to as model UC-2 Epilator.

In any event, the electrolysis device 22 includes a ground line 23 that leads from the electrolysis device 22 to a ground terminal 24, which in the present case may be a conductive patch, plate, or probe that may be engaged with the skin in or in the vicinity of the localized treatment area. Alternatively, a conventional ground terminal, such as a hand-held device, may be used and engaged with the person remote from the area to be treated.

In addition, the electrolysis device 22 includes a current line 26 that leads from the electrolysis device 22 to an electric probe terminal 28. The electric probe terminal 28 shown in this embodiment comprises a metal tube 30 having an absorbent material 36 such as sponge, foam, or cotton at one end. For example, the stem of a "Q-tip" may be inserted into the tube 30 with the cotton swab of the Q-tip extending out the end of the tube 30. At the other end, the probe 28 includes an insulated hand holding portion 34. Prior to electrolysis, the absorbent material 36 is saturated with an electrode solution 38 in a large enough quantity that the solution can be dispensed from the absorbent material 36 and applied to the localized treatment area of the skin, as will be explained below. Alternatively, the electrified terminal may be a metallic plate or patch that is shaped to conform to the area of skin from which hair is to be removed.

In the present case, the electrode solution is a conventional aqueous solution containing dissolved electrolytes. A typical electrode solution used in the method of the invention may comprise water, sodium myreth sulfate, sodium lauroamphoacetate, cocamidopropyl betaine, panthenol, phytantriol, DMDM hydantoin, trisodium EDTA, citric acid, and sodium chloride.

Now, turning to the particular surface electrolysis method of the present invention, a particular localized area of skin from which hair is to be removed, indicated by the number 40, is selected. In the drawings, the localized treatment area is shown on a person's face surrounding the mouth so as to perform electrolysis around the lips, although the electrolysis process can just as easily be performed anywhere else on the person's body. It is contemplated that a particular localized treatment area 40 could be up to approximately four to five inches across and could encompass up to approximately fifteen square inches of skin.

The ground terminal 24 is then engaged with the skin, here shown within the localized area 40, in such a way as to ensure good electrical conductivity. Next, the electrolysis device 22 is actuated so as to direct an electric current to the electric probe terminal 28. The probe terminal 28 is touched to the skin 14 so that the absorbent material 36 contacts the skin 14 and applies electrode solution 38 thereon. The absorbent material 36 of the probe terminal 28 is touched to the skin 14 to apply the electrode solution 38 and simultaneously direct electric current to approximately a one-quarter inch square micro-area 42 of the localized treatment area 40. After the first micro-area 42 is treated, the electrified probe 28 may then be advanced to successive micro-areas of the localized treatment area 40 to perform electrolysis in those micro-areas also.

In a preferred method of treating each micro-area, a close relationship is maintained between the electrified probe terminal 28 and the ground terminal 24 such that during electrolysis, the probe terminal 28 and the ground terminal 24 are not separated by any distance substantially greater than the greatest width of the localized treatment area 40. In the present embodiment, this distance is contemplated as being up to approximately four to five inches. The reason for maintaining this close proximity between the electrified probe terminal 28 and the ground terminal 24 is to enhance the efficiency of the electric current passing through the patient's body by reducing the dispersion of electricity that can result from separating the probe terminal 28 and the ground terminal 24 in conventional fashion. This increased electrical efficiency oftentimes produces more effective electrolysis of hairs in the localized area and therefore reduces the need for some patients to undergo repeat electrolysis sessions.

While the ground terminal 24 may remain affixed to the skin in one spot during the treatment, it also may be moved along with the electrified probe terminal 28 during electrolysis of successive micro-areas to maintain a constant distance between the two terminals 24, 28. This is particularly the case when the ground terminal 24 consists of a probe like the preferred embodiment of the electrified terminal 28. It is even contemplated that the two terminals 24, 28 may be combined into a single hand held unit having two electrically isolated terminals spaced slightly apart and extending therefrom. However, if desired, the present method of non-invasive surface electrolysis may be carried out using a conventional ground terminal held in the hand or otherwise remotely engaged with the patient's body.

In the present electrolysis process, the activating current is a DC current of approximately 2000 microamps and approximately 380 volts. This small current is directed to each micro-area of the skin for anywhere from 1 second to 3 minutes (preferable about 1 minute). The electrode solution coating the skin acts as a conductor of electricity. The electric current is conducted through the soft moist tissue 20 surrounding the hairs 16 downwardly to the hair follicles 18, which contain salt water, whereupon the electrolysis process occurs. Thereafter, the hairs are allowed to stand for a selected time period to allow the sodium hydroxide produced to effect follicle decomposition. In some patients, it has been shown that a time of approximately one minute is sufficient. After such time, the hairs are easily extracted from the patient's skin.

The present invention may, of course, be carried out in other specific ways than those herein set forth without departing from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A non-invasive method of treating hair on a person's skin by skin surface electrolysis, comprising the steps of:
   (a) selecting a localized treatment area of skin from which hair is to be removed;
   (b) engaging a ground terminal of an electrolysis device with the person;
   (c) touching an electrified probe terminal of the electrolysis device directly to the surface of the skin within the localized treatment area without in any way penetrating the skin's surface;
   (d) conducting a DC electric current from the electrified probe terminal into and through the skin and hair follicles of the localized treatment area; and
   (e) producing sodium hydroxide in the hair follicles by ionizing water and sodium chloride in the presence of the DC electric current, causing the germ cells of the hair follicles to die, and resulting in the hair follicles decomposing.

2. The method of claim 1 wherein the probe terminal includes an electron transfer medium, and further including the step of placing the electron transfer medium of the probe terminal onto the skin to facilitate the transfer of electricity from the probe terminal to the skin.

3. The method of claim 2 wherein the electron transfer medium includes an absorbent applicator, and further including the step of saturating the absorbent applicator with an electrode solution.

4. The method of claim 1 wherein the ground terminal contacts the person in the vicinity of the localized treatment area so that during electrolysis, the electrified probe terminal and the ground terminal are not separated by any distance substantially greater than the greatest width of the localized treatment area.

5. The method of claim 1, further including the step of applying an electrode solution to the localized treatment area of skin to facilitate the transfer of electrical current from the probe terminal to the skin.

6. The method of claim 5, wherein the step of applying the electrode solution to the localized treatment area of the skin occurs while simultaneously conducting the DC current from the electrified probe terminal into the localized skin treatment area.

7. The method of claim 1, further including the step of allowing hairs to remain in the hair follicles for a selected time period after being treated.

8. The method of claim 7, wherein the hairs are allowed to remain in the hair follicles for approximately one minute after being treated.

9. The method of claim 1, further including the step of removing hairs from the hair follicles.

10. The method of claim 1, further including the step of moving the electrified probe terminal to successive localized treatment areas of skin to perform skin surface electrolysis in those successive localized treatment areas.

11. The method of claim 10, further including the step of moving the ground terminal after performing skin surface electrolysis in each localized treatment area so as to maintain a substantially constant distance between the ground terminal and the electrified probe terminal.

12. The method of claim 1, further including the step of securing an absorbent applicator tip to the electrified probe terminal and saturating the absorbent tip with an electrode solution.

13. The method of claim 12, further including the step of applying the electrode solution onto the localized skin treatment area while the DC electric current is conducted into the localized skin treatment area.

14. The method of claim 1, wherein the step of conducting the DC electric current into the localized treatment area includes conducting a relatively high voltage but small current through the skin and hair follicles for a selected period of time.

15. The method of claim 1, wherein the localized treatment area includes up to approximately fifteen square inches of skin surface.

* * * * *